US007250512B2

(12) United States Patent
Lecloux et al.

(10) Patent No.: US 7,250,512 B2
(45) Date of Patent: Jul. 31, 2007

(54) ELECTROLUMINESCENT IRIDIUM COMPOUNDS HAVING RED-ORANGE OR RED EMISSION AND DEVICES MADE WITH SUCH COMPOUNDS

(75) Inventors: Daniel David Lecloux, Wilmington, DE (US); Viacheslav A. Petrov, Hockessin, DE (US); Ying Wang, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 86 days.

(21) Appl. No.: 10/284,593

(22) Filed: Oct. 31, 2002

(65) Prior Publication Data

US 2003/0096138 A1 May 22, 2003

Related U.S. Application Data

(60) Provisional application No. 60/347,911, filed on Nov. 7, 2001.

(51) Int. Cl.
C09K 11/06 (2006.01)
H01L 51/54 (2006.01)

(52) U.S. Cl. .................... 546/4; 546/10; 548/402; 544/179; 544/181; 544/225; 428/690; 428/917; 313/504; 257/102; 257/103; 257/E51.044

(58) Field of Classification Search ................ 428/690, 428/917; 313/504, 506; 257/88, 102, 103; 546/4, 10; 252/301.16; 548/402; 549/3; 544/179, 181, 225
See application file for complete search history.

(56) References Cited

U.S. PATENT DOCUMENTS

| 3,718,488 | A | 2/1973 | Trofimenko et al. | |
| 5,552,678 | A | 9/1996 | Tang et al. | |
| 6,303,238 | B1 | 10/2001 | Thompson et al. | 428/690 |
| 6,576,352 | B2 * | 6/2003 | Hirai | 428/690 |
| 6,670,645 | B2 | 12/2003 | Grushin et al. | 257/98 |
| 2001/0019782 | A1 | 9/2001 | Igarashi et al. | 428/690 |
| 2001/0053462 | A1 | 12/2001 | Mishima | 428/690 |
| 2002/0064681 | A1 | 5/2002 | Takiguchi et al. | 428/690 |
| 2002/0182441 | A1 | 12/2002 | Lamansky et al. | 428/690 |
| 2003/0059646 | A1 | 3/2003 | Kamatani et al. | 428/690 |
| 2003/0068526 | A1 | 4/2003 | Kamatani et al. | 428/690 |
| 2003/0072964 | A1 | 4/2003 | Kwong et al. | 428/690 |
| 2003/0108771 | A1 | 6/2003 | LeCloux et al. | 428/690 |

FOREIGN PATENT DOCUMENTS

| EP | 1175128 A2 | 1/2002 |
| EP | 1 191 612 A2 | 3/2002 |
| WO | WO 00/70655 A2 | 11/2000 |
| WO | WO 01/41512 A1 | 6/2001 |
| WO | WO 02/02714 A2 | 1/2002 |
| WO | WO 02/15645 A1 | 2/2002 |
| WO | WO 02/44189 A1 | 6/2002 |
| WO | WO 03/063555 A1 | 7/2003 |

OTHER PUBLICATIONS

Lamansky, Sergey et al., Highly Phosphorescent Bis-Cyclometalated Iridium Complexes: Synthesis, Photophysical Characterization, and Use in Organic Light Emitting Devices, J. Am. Chem. Soc., 2001, 4304-4312, 123, American Chemical Society.
Lamansky, Sergey et al., Synthesis and Characterization of Phosphorescent Cyclometalated Iridium Complexes, Inorg. Chem., 2001, 1704-1711, 40, American Chemical Society, published on web Mar. 1, 2001.
Djurovich, Peter I. et al., Ir(III) Cyclometalated Complexes As Efficient Phosphorescent Emitters In Polymer Blend and Organic LEDs, Polymer Preprints, 2000,770-771, 41(1).
Lamansky, Sergey et al., Molecularly doped polymer light emitting diodes utilizing phosphorescent Pt(II) and IR(III) dopants, Organic Electronics, 2001, 53-62, 2, Elsevier Science B.V.
Chatani, Naoto et al., Ru3(CO)12-Catalyzed Reaction of Pyridylbenzenes with Carbon Monoxide and Olefins. Carbonylation at a C—H Bond in the Benzene Ring, J. Org. Chem., 1997, 2604-2610, 62, American Chemical Society.
Gosmini, Corinne et al., Electrosynthesis of functionalized 2-arylpyridines from functionalized aryl and pyridine halides catalyzed by nickel bromide 2,2'-bipyridine complex, Tetrahedron Letters, 2000, 5039-5042, 41, Elsevier Science Ltd.
Cacchi, Sandro et al., The Palladium-Catalyzed Transfer Hydrogenation/Heterocyclization of B-(2-Aminophenyl-a,B-ynones. An Approach to 2-Aryl- and 2-Vinylquinolines, Synlett, 1999, 401-414, No. 4, Thieme Stuttgart, New York.
Baldo, M. A. et al., Very high-efficiency green organic light-emitting devices based on electrophosphorescence, Applied Physics Letters, Jul. 5, 1999, 4-6, 75(1) American Institue of Physics.
Baldo, M. A. et al., High-efficiency fluorescent organic light-emitting devices using a phosphorescent sensitizer, Nature, Feb. 17, 2000, 750-753, 403, Macmillan Magazines Ltd.
Wang, Yue et al., (Hydroxyphenyl)pyridine derivative, its metal complexes and application as electroluminescence material, Chemical Abstracts Service, Mar. 1, 2000, Database No. 133:315395.
Dedeian K. et al., A New Synthetic Route to the Preparation of a Series of Strong Photoreducing Agents: fac Tris-Ortho-Metalated Complexes of Iridium(III) with Substituted 2-Phenylpyridines, Inorg. Chem., 1991, 1685-1687, 30(8), American Chemical Society.
Baldo, M.A. et al., Highly efficient phosphorescent emission from organic electroluminescent devices, Nature, Sep. 10, 1998, 151-154, vol. 395.
Lohse, Oliver et al., The Palladium Catalysed Suzuki Coupling of 2- and 4-Chloropyridines, Synlett, 1999, 45-48, No. 1, Thieme Suttgart, New York.
Abstract of Japanese PCT Publication WO02/44189 A1, Luminescent Element and Display, Jun. 6, 2002, Canon Kabushiki Kaisha (same family as US 2003/0068526 A1).
Abstract of German PCT Publication WO96/03410, Hydrophilic Metal Complexes, Feb. 8, 2006, Boehringer Mannheim GmbH.

* cited by examiner

Primary Examiner—Marie Yamnitzky
(74) Attorney, Agent, or Firm—John H. Lamming

(57) ABSTRACT

The present invention is generally directed to electroluminescent Ir(III) complexes which have emission maxima in the red-orange to red region of the visible spectrum and devices that are made with the Ir(III) complexes.

5 Claims, 5 Drawing Sheets

(III)

(IV)

(V)

(VI)

(VII)

$Q = B(OH)_2$ or $MgBr$

Eq. (2)

Eq. (3)

Eq. (4)

ELECTROLUMINESCENT IRIDIUM COMPOUNDS HAVING RED-ORANGE OR RED EMISSION AND DEVICES MADE WITH SUCH COMPOUNDS

This application claims priority to provisional application, Ser. No. 60/347,911, dated Nov. 7, 2001.

BACKGROUND OF THE INVENTION

1. Field of the Invention

This invention relates to electroluminescent complexes of iridium(III) which have emission spectra in the red-orange and red region of the visible spectrum. It also relates to electronic devices in which the active layer includes an electroluminescent Ir(III) complex.

2. Description of the Related Art

Organic electronic devices that emit light, such as light-emitting diodes that make up displays, are present in many different kinds of electronic equipment. In all such devices, an organic active layer is sandwiched between two electrical contact layers. At least one of the electrical contact layers is light-transmitting so that light can pass through the electrical contact layer. The organic active layer emits light through the light-transmitting electrical contact layer upon application of electricity across the electrical contact layers.

It is well known to use organic electroluminescent compounds as the active component in light-emitting diodes. Simple organic molecules such as anthracene, thiadiazole derivatives, and coumarin derivatives are known to show electroluminescence. Semiconductive conjugated polymers have also been used as electroluminescent components, as has been disclosed in, for example, Friend et al., U.S. Pat. No. 5,247,190, Heeger et al., U.S. Pat. No. 5,408,109, and Nakano et al., Published European Patent Application 443 861. Complexes of 8-hydroxyquinolate with trivalent metal ions, particularly aluminum, have been extensively used as electroluminescent components, as has been disclosed in, for example, Tang et al., U.S. Pat. No. 5,552,678.

Electroluminescent devices with an active layer of polymer doped with organometallic complexes of iridium have been described by Burrows and Thompson in published PCT applications WO 00/70655 and WO 01/41512. Most of these complexes have emission spectra with peaks in the green or blue-green region.

There is a continuing need for efficient electroluminescent compounds which emit light in the red region of the visible spectrum (625-700 nm)

SUMMARY OF THE INVENTION

The present invention is directed to a metal complex having a formula selected from Formula I and Formula II:

    (I)

    (II)

Where:

Z is selected from β-dienolates, aminocarboxylates, iminocarboxylates, salicylates, hydroxyquinolates, and diarylphosphinoalkoxides; and L is selected from Formula III, Formula IV, Formula V, Formula VI, and Formula VII in FIG. 1, and Formula VIII, Formula IX and Formula X in FIG. 2, where:

in Formula II:

$R^3$ through $R^6$ are the same or different and at least one of $R^3$ through $R^6$ is selected from D, F, $C_nF_{2n+1}$, $OC_nF_{2n+1}$, and $OCF_2Y$;

at each occurrence in any of Formulae III through VII:
$R^1$ is the same or different at each occurrence and is selected from D, $C_nH_{2n+1}$, $OR^{11}$, $SR^{11}$, $N(R^{11})_2$, F, $C_n(H+F)_{2n+1}$, $OC_n(H+F)_{2n+1}$, and $OCF_2Y$, or adjacent pairs of $R^1$ can be joined to form a five- or six-membered ring;
Y is H, Cl, or Br; and
A is S or $NR^{11}$;

at each occurrence in any of Formulae III through X:
$R^{11}$ is the same or different at each occurrence and is H or $C_nH_{2n+1}$;
n is an integer from 1 through 12; and
α is 0, 1 or 2;

at each occurrence in any of Formulae IV through X:
δ is 0 or an integer from 1 through 4;

in Formula VII:
$E^1$ through $E^4$ are the same or different and are N or $CR^{12}$, with the proviso that at least one E is N; and
$R^{12}$ is the same or different at each occurrence and is selected from H, D, $SR^{11}$, $N(R^{11})_2$, F, $C_n(H+F)_{2n+1}$, $OC_n(H+F)_{2n+1}$, and $OCF_2Y$, or adjacent pairs of $R^{12}$ can be joined to form a five- or six-membered ring, with the proviso that at least one of $R^{12}$ is selected from D, F, $C_n(H+F)_{2n+1}$, $OC_n(H+F)_{2n+1}$, and $OCF_2Y$;

at each occurrence in any of Formulae VIII through X:
$R^2$ and $R^7$ through $R^{10}$ are the same or different at each occurrence and are selected from H, D, $C_nH_{2n+1}$, $OR^{11}$, $SR^{11}$, and $N(R^{11})_2$, or adjacent pairs of R groups can be joined to form a five- or six-membered ring.

In another embodiment, the present invention is directed to an organic electronic device having at least one active layer comprising a light-emitting layer having an emission maximum in the range of from 570 to 700 nm, wherein at least 20% by weight of the active layer comprises the above metal complex, or combinations of the above metal complexes.

As used herein, the term "compound" is intended to mean an electrically uncharged substance made up of molecules that further consist of atoms, wherein the atoms cannot be separated by physical means. The term "ligand" is intended to mean a molecule, ion, or atom that is attached to the coordination sphere of a metallic ion. The letter "L" is used to designate a ligand having a nominal (−1) charge formed from the neutral parent compound, "HL", by the loss of a hydrogen ion. The letter "Z" is used to designate a bidentate ligand having a nominal (−1) charge formed from the neutral parent compound, "HZ", by the loss of a hydrogen ion. The term "complex", when used as a noun, is intended to mean a compound having at least one metallic ion and at least one ligand. The term "β-dicarbonyl" is intended to mean a neutral compound in which two ketone groups are present, separated by a CHR group. The term "β-enolate" is intended to mean the anionic form of the β-dicarbonyl in which the H from the CHR group between the two carbonyl groups has been abstracted. The term "group" is intended to mean a part of a compound, such a substituent in an organic compound or a ligand in a complex. The term "facial" is intended to mean one isomer of a complex, $Ma_3b_3$, having octahedral geometry, in which the three "a" groups are all adjacent, i.e. at the corners of one face of the octahedron. The term "meridional" is intended to mean one isomer of a complex, $Ma_3b_3$, having octahedral geometry, in which the three "a" groups occupy three positions such that two are trans to each other. The phrase "adjacent to," when used to refer to layers in a device, does not necessarily mean that one layer is immediately next to another layer. On the other hand, the phrase "adjacent R groups," is used to refer to R groups that are next to each other in a chemical formula (i.e., R groups that are on atoms joined by a bond). The term "photoactive" refers to any material that exhibits electroluminescence and/or photosensitivity. In addition, the IUPAC numbering system is used throughout, where the groups from the Periodic Table are numbered from left to right as 1 through 18 (CRC Handbook of Chemistry and Physics, 81$^{st}$ Edition, 2000). In the Formulae and Equations, the letters A, E, L, R, Q, Y and Z are used to designate atoms or groups which are defined within. All other letters are used to designate conventional atomic symbols. The term "(H+F)" is intended to mean all combinations of hydrogen and fluorine, including completely hydrogenated, partially fluorinated or perfluorinated substituents. By "emission maximum" is meant the wavelength, in nanometers, at which the maximum intensity of electroluminescence is obtained.

Electroluminescence is generally measured in a diode structure, in which the material to be tested is sandwiched between two electrical contact layers and a voltage is applied. The light intensity and wavelength can be measured, for example, by a photodiode and a spectrograph, respectively.

DETAILED DESCRIPTION OF THE PREFERRED EMBODIMENTS

The metal complexes of the invention have one of Formulae I and II given above, and are referred to as cyclometallated complexes. The iridium in Formulae I and II is in the +3 oxidation state and is hexacoordinate. In Formula I, the complex is a tris-cyclometallated complex with no additional ligands. The tris complexes may exhibit a facial or a meridional geometry, but most often the facial isomer is formed. In Formula II, the complex is a bis-cyclometallated complex with an additional monoanionic bidentate ligand, Z. These cyclometallated iridium complexes are neutral and non-ionic, and can be sublimed intact. Thin films of these materials obtained via vacuum deposition exhibit good to excellent electroluminescent properties.

The complexes of the invention have emission spectra with maxima in the range of 570 to 700 nm, which is in the red-orange to red region of the visible spectrum. The preferred red emission is at 620 nm and above.

Figure 1:
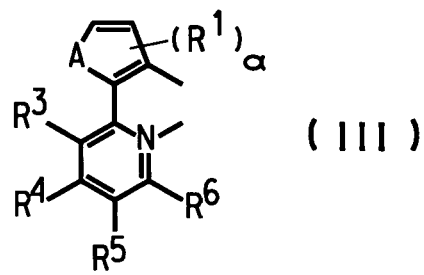
FIG. 1 shows Formulae III through VII for the ligand L useful in the metal complex of the invention.
Figure 1:
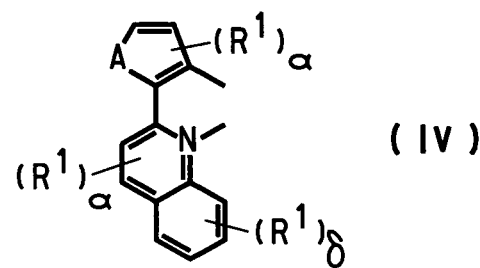
Figure 1:
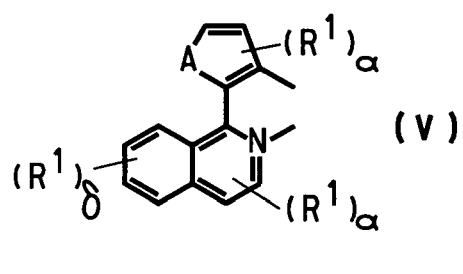
Figure 1:
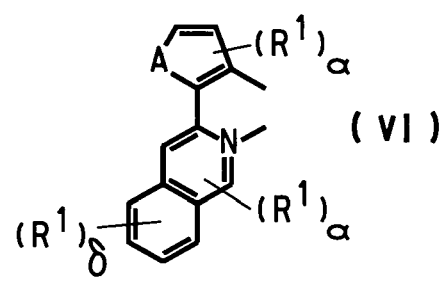
Figure 1:
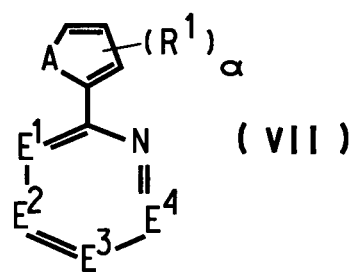

Ligand L having Formula II, shown in FIG. 1, is derived from a thienyl-pyridine (when A is S) or pyrrolyl-pyridine (when A is $NR^{11}$) compound in which there is at least one fluorine-containing substituent on the pyridine ring. The $R^3$ through $R^6$ groups may be chosen from conventional substitutents for organic compounds, such as alkyl, alkoxy, halogen, nitro, and cyano groups, as well as deutero, fluoro, fluorinated alkyl and fluorinated alkoxy groups. The groups can be partially or fully fluorinated (perfluorinated). It is preferred that α is 0, and that $R^3$ and/or $R^5$ is a fluorine-containing substitutent. Most preferred is $CF_3$. When A is $NR^{11}$, it is preferred that $R^{11}$ is $CH_3$.

Ligand L having Formula IV, shown in FIG. 1, is derived from a thienyl- or a pyrrolyl-quinoline compound. Ligand L having Formula V or Formula VI, shown in FIG. 1, is derived from a thienyl- or a pyrrolyl-isoquinoline compound. It is preferred that alpha is 0. When A is $NR^{11}$, it is preferred that $R^{11}$ is $CH_3$.

Ligand L having Formula VII, shown in FIG. 1, is derived from a thienyl- or a pyrrolyl-diazine compound, or the analog with 3 or more nitrogens. There is at least one substituent on the 6-membered ring that is selected from D (deuterium), F, $C_n(H+F)_{2n+1}$, $OC_n(H+F)_{2n+1}$, and $OCF_2Y$, most preferably $CF_3$. It is preferred that α is 0. When A is $NR^{11}$, it is preferred that $R^{11}$ is $CH_3$.

Figure 2:
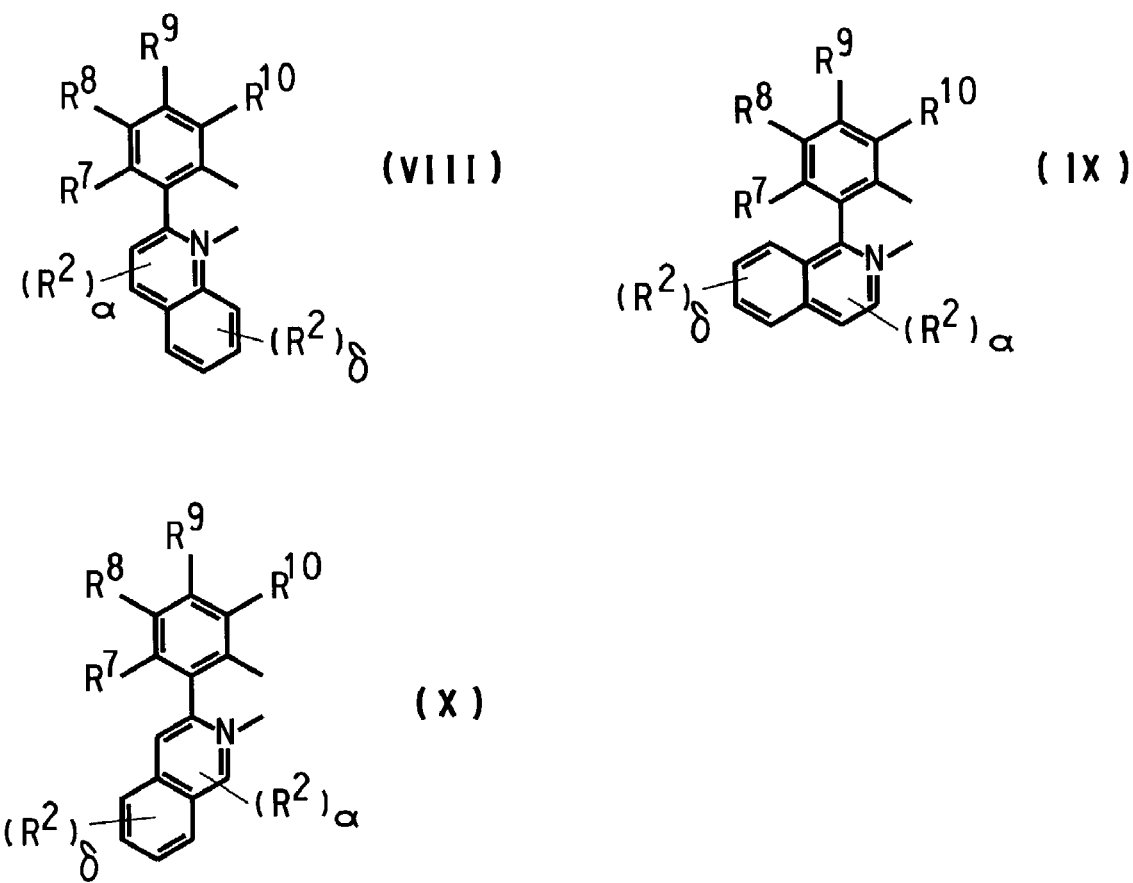
FIG. 2 shows Formulae VIII through X for the ligand L useful in the metal complex of the invention.

Ligand L having Formula VIII, shown in FIG. 2, is derived from a phenyl-quinoline compound. Ligand L having Formulae IX or X, shown in FIG. 2, is derived from a phenyl-isoquinoline compound. The $R^7$ through $R^{10}$ groups may be chosen from conventional substitutents for organic compounds, such as alkyl, alkoxy, halogen, nitro, and cyano groups, as well as deutererium. It is preferred that the $R^8$ and/or $R^{10}$ is a substituent bonded through a heteroatom having non-bonding pi electrons, most preferably oxygen. It is preferred that the $R^9$ substituent is an alkyl, preferably a tertiary alkyl.

Figure 4:
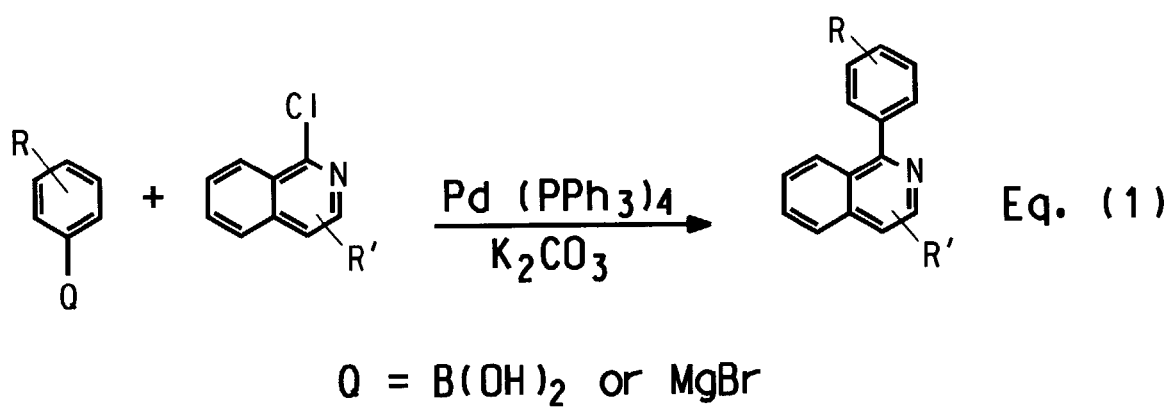
FIG. 4 shows Equation (1) for synthesis of the parent ligand compounds, HL, useful in the invention.

The parent ligand compounds, HL, can generally be prepared by standard palladium-catalyzed Suzuki or Kumada cross-coupling of the corresponding heterocyclic aryl chloride with an organoboronic acid or organomagnesium reagent, as described in, for example, O. Lohse, P. Thevenin, E. Waldvogel *Synlett,* 1999, 45-48. This reaction is illustrated for a phenyl-isoquinoline, where R and $R^1$ represent substituents, in Equation (1) in FIG. 4.

The Z ligand is a monoanionic bidentate ligand. In general these ligands have N, O, P, or S as coordinating atoms and form 5- or 6-membered rings when coordinated to the iridium. Suitable coordinating groups include amino, imino, amido, alkoxide, carboxylate, phosphino, thiolate, and the like. Examples of suitable parent compounds for these ligands include β-dicarbonyls (β-enolate ligands), and their N and S analogs; amino carboxylic acids (aminocarboxylate ligands); pyridine carboxylic acids (iminocarboxylate ligands); salicylic acid derivatives (salicylate ligands); hydroxyquinolines (hydroxyquinolinate ligands) and their S analogs; and diarylphosphinoalkanols (diarylphosphinoalkoxide ligands).

Figure 3:
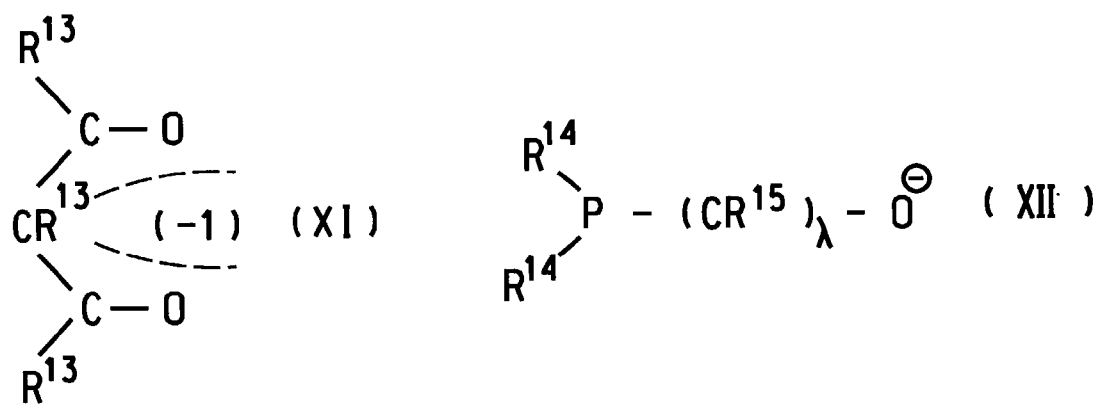
FIG. 3 shows Formula XI for the β-enolate ligand and Formula XII for the phosphino alkoxide ligand, useful in the invention.

The β-enolate ligands generally have Formula XI shown in FIG. 3, where $R^{13}$ is the same or different at each occurrence. The $R^{13}$ groups can be hydrogen, halogen, substituted or unsubstituted alkyl, aryl, alkylaryl or heterocyclic groups. Adjacent $R^{13}$ groups can be joined to form five- and six-membered rings, which can be substituted. Preferred $R^{13}$ groups are selected from H, F, $C_n(H+F)_{2n+1}$, $-C_6H_5$, $-C_4H_3S$, and $-C_4H_3O$, where n is an integer from 1 to 12, preferably from 1 to 6.

Examples of suitable β-enolate ligands, Z, include the compounds listed below. The abbreviation for the β-enolate form is given below in brackets.

2,4-pentanedionate [acac]
1,3-diphenyl-1,3-propanedionate [DI]
2,2,6,6-tetramethyl-3,5-heptanedionate [TMH]
4,4,4-trifluoro-1-(2-thienyl)-1,3-butanedionate [TTFA]
7,7-dimethyl-1,1,1,2,2,3,3-heptafluoro-4,6-octanedionate [FOD]
1,1,1,3,5,5,5-heptafluoro-2,4-pentanedionate [F7acac]
1,1,1,5,5,5-hexaflouro-2,4-pentanedionate [F6acac]
1-phenyl-3-methyl-4-i-butyryl-pyrazolinonate [FMBP]

The β-dicarbonyl parent compounds, HZ, are generally available commercially. The parent compound of F7acac, 1,1,1,3,5,5,5-heptafluoro-2,4-pentanedione, $CF_3C(O)CFHC(O)CF_3$, can be prepared using a two-step synthesis, based on the reaction of perfluoropentene-2 with ammonia, followed by a hydrolysis step. This compound should be stored and reacted under anyhydrous conditions as it is susceptible to hydrolysis.

The hydroxyquinoline parent compounds, HZ, can be substituted with groups such as alkyl or alkoxy groups which may be partially or fully fluorinated. In general, these compounds are commercially available. Examples of suitable hydroxyquinolinate ligands, Z, include:

8-hydroxyquinolinate [8hq]
2-methyl-8-hydroxyquinolinate [Me-8hq]
10-hydroxybenzoquinolinate [10-hb]

The parent hydroxyquinoline compounds are generally available commercially.

The phosphino alkoxide parent compounds, HZ, generally have Formula XII, shown in FIG. 3, where $R^{14}$ can be the same or different at each occurrence and is selected from $C_n(H+F)_{2n+1}$ and $C_6(H+F)_5$,
$R^{15}$ can be the same or different at each occurrence and is selected from H and $C_n(H+F)_{2n+1}$, and
λ is 2 or 3.

Examples of suitable phosphino alkoxide ligands listed below. The abbreviation for these ligands is given below in brackets.

3-(diphenylphosphino)-1-oxypropane [dppo]
1,1-bis(trifluoromethyl)-2-(diphenylphosphino)-ethoxide [tfmdpeO]

The parent phosphino alkanol compounds are generally available commercially.

Figure 5:
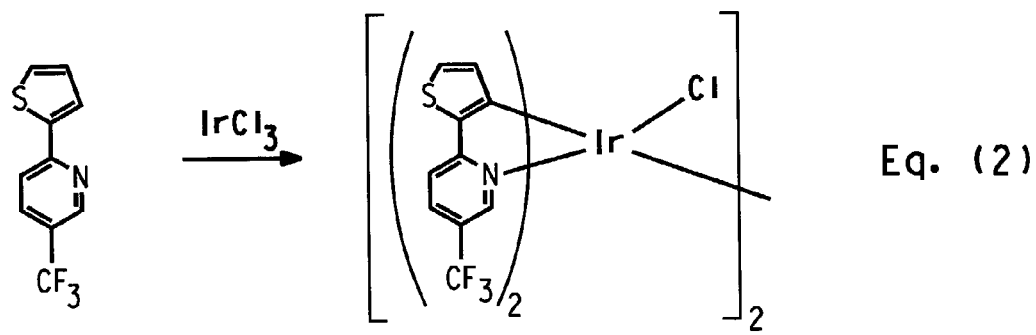
FIG. 5 shows Equations (2) through (4) for forming the complexes useful in the invention.
Figure 5:
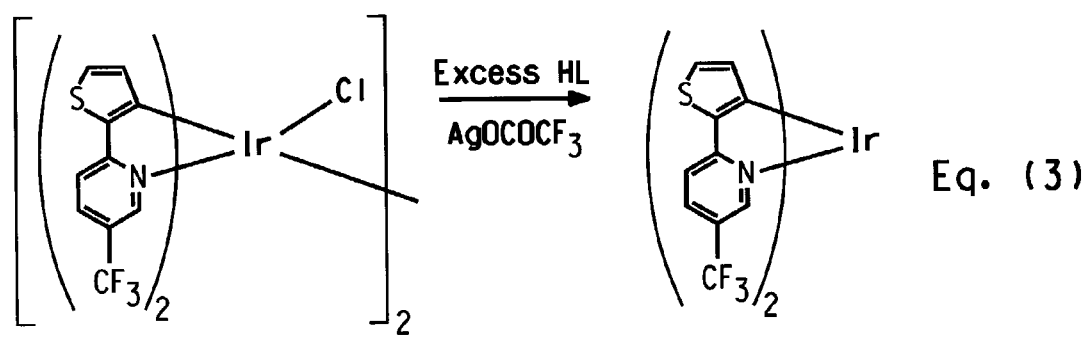
Figure 5:
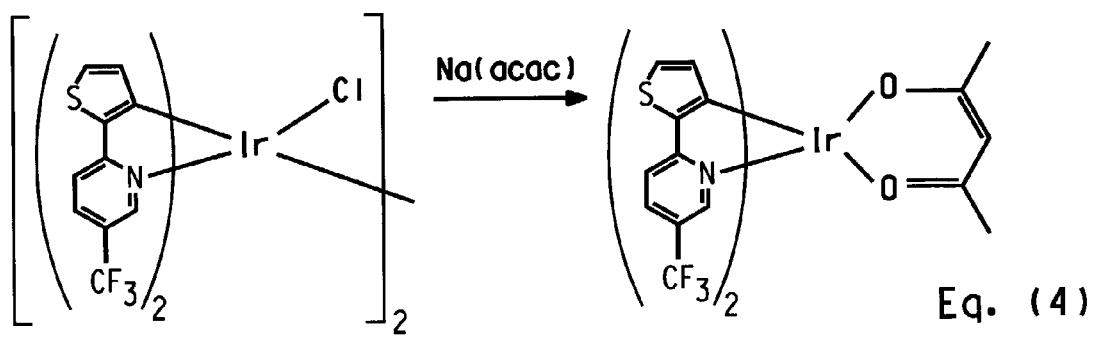

Complexes of Formulae I and II are generally prepared from the metal chloride salt by first forming the bridged chloride dimer. This reaction is illustrated for a thienylpyridine ligand in Equation (2) shown in FIG. 5. Complexes of Formula I are then formed by adding an excess of the ligand parent compound HL, without a solvent, in the presence of 2 equivalents of silver trifluoroacetate, $AgO-COCF_3$, per dimer. This reaction is illustrated in Equation (3) in FIG. 5. Complexes of Formula II are formed by adding the sodium salt of the Z ligand to the bridged chloride dimer. This reaction is illustrated in Equation (4) in FIG. 5.

Examples of metal complexes of the invention are given in Table 1 below. At each occurrence, α and δ are zero.

TABLE 1

| Complex | Complex Formula | Ligand Formula | A | R substituents | Z |
|---|---|---|---|---|---|
| 1-a | I | III | S | $R^5 = CF_3$ | — |
| 1-b | I | V | S | none | — |
| 1-c | I | IX | — | $R^9$ = t-butyl | — |
| 1-d | I | IX | — | $R^8 = OCH_3$ | — |
| 1-e | I | IX | — | $R^8$ = OH | — |
| 1-f | I | VIII | — | $R^9$ = t-butyl | — |
| 1-g | II | III | N—$CH_3$ | $R^5 = CF_3$ | acac |
| 1-h | II | V | S | none | acac |
| 1-i | II | IX | — | none | acac |
| 1-j | II | IX | — | $R^9$ = t-butyl | acac |
| 1-k | II | IX | — | $R^8 = OCH_3$ | acac |
| 1-l | II | VIII | — | $R^9$ = t-butyl | acac |
| 1-m | II | IX | — | $R^7 = R^8 = R^9 = R^{10}$ = D | acac |

The complexes in Table 1 have electroluminescent emission maxima from about 570 nm, for compound 1-a, to about 670 nm, for compound 1-k.

Electronic Device

Figure 6:
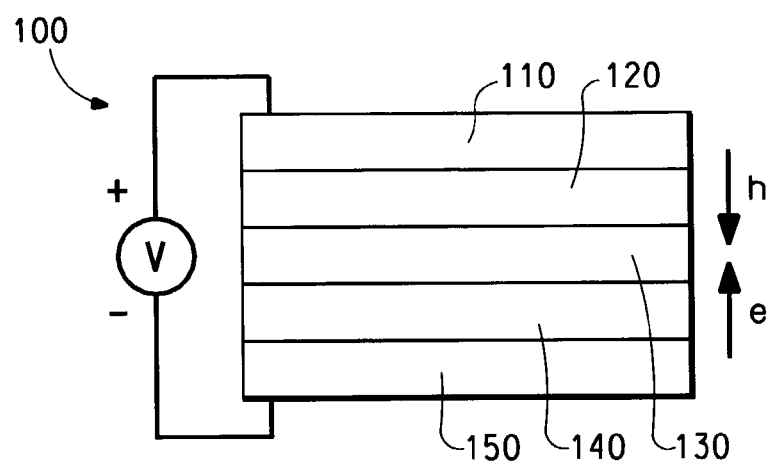
FIG. 6 is a schematic diagram of a light-emitting device (LED).

The present invention also relates to an electronic device comprising at least one photoactive layer positioned between two electrical contact layers, wherein the at least one photoactive layer of the device includes the complex of the invention. As shown in FIG. 6, a typical device 100 has an anode layer 110 and a cathode layer 150 and layers 120, 130 and optionally 140 between the anode 110 and cathode 150. Layers 120, 130, and 140 are collectively referred to as the active layers. Adjacent to the anode is a hole injection/transport layer 120. Adjacent to the cathode is an optional layer 140 comprising an electron transport material. Between the hole injection/transport layer 120 and the cathode (or optional electron transport layer) is the photoactive layer 130. Layers 120, 130, and 140 are individually and collectively referred to as the active layers.

Depending upon the application of the device 100, the photoactive layer 130 can be a light-emitting layer that is activated by an applied voltage (such as in a light-emitting diode or light-emitting electrochemical cell), a layer of material that responds to radiant energy and generates a signal with or without an applied bias voltage (such as in a photodetector). Examples of photodetectors include photoconductive cells, photoresistors, photoswitches, phototransistors, and phototubes, and photovoltaic cells, as these terms are describe in Markus, John, *Electronics and Nucleonics Dictionary*, 470 and 476 (McGraw-Hill, Inc. 1966).

The complexes of the invention are particularly useful as the photoactive material in layer 130, or as electron transport material in layer 140. When used in layer 130, it has been found that the complexes of the invention do not need to be in a solid matrix diluent in order to be effective. A layer that is greater than 20% by weight metal complex, based on the total weight of the layer, up to 100% metal complex, can be used as the emitting layer. Additional materials can be present in the emitting layer with the metal complex. For example, a fluorescent dye may be present to alter the color of emission. A diluent may also be added. Preferably, the diluent facilitates charge transport in the layer. The diluent can be a polymeric material, such as poly(N-vinyl carbazole) and polysilane. It can also be a small molecule, such as 4,4'-N,N'-dicarbazole biphenyl or tertiary aromatic amines. When a diluent is used, the metal complex is generally present in a small amount, usually less than 20% by weight, preferably less than 10% by weight, based on the total weight of the layer.

One type of diluent which is useful with the iridium metal complexes of the invention, is a conjugated polymer in which the triplet excited state of the polymer is at a higher energy level than the triplet excited state of the iridium complex. Examples of suitable conjugated polymers include polyarylenevinylenes, polyfluorenes, polyoxadiazoles, polyanilines, polythiophenes, polypyridines, polyphenylenes, copolymers thereof, and combinations thereof. The conjugated polymer can be a copolymer having non-conjugated portions of, for example, acrylic, methacrylic, or vinyl, monomeric units. Particularly useful are homopolymers and copolymers of fluorene and substituted fluorenes.

In some cases the metal complexes of the invention may be present in more than one isomeric form, or mixtures of different complexes may be present. It will be understood that in the above discussion of OLEDs, the term "the metal complex" is intended to encompass mixtures of complexes and/or isomers.

The device generally also includes a support (not shown) which can be adjacent to the anode or the cathode. Most frequently, the support is adjacent the anode. The support can be flexible or rigid, organic or inorganic. Generally, glass or flexible organic films are used as a support. The anode 110 is an electrode that is particularly efficient for injecting or collecting positive charge carriers. The anode is preferably made of materials containing a metal, mixed metal, alloy, metal oxide or mixed-metal oxide. Suitable metals include the Group 11 metals, the metals in Groups 4, 5, and 6, and the Group 8-10 transition metals. If the anode is to be light-transmitting, mixed-metal oxides of Groups 12, 13 and 14 metals, such as indium-tin-oxide, are generally used. The anode 110 may also comprise an organic material such as polyaniline as described in "Flexible light-emitting diodes made from soluble conducting polymers," *Nature* vol. 357, pp 477-479 (Jun. 11, 1992).

The anode layer 110 is usually applied by a physical vapor deposition process or spin-cast process. The term "physical vapor deposition" refers to various deposition approaches carried out in vacuo. Thus, for example, physical vapor deposition includes all forms of sputtering, including ion beam sputtering, as well as all forms of vapor deposition such as e-beam evaporation and resistance evaporation. A specific form of physical vapor deposition which is useful is rf magnetron sputtering.

There is generally a hole transport layer 120 adjacent the anode. Examples of hole transport materials for layer 120 have been summarized for example, in Kirk-Othmer *Encyclopedia of Chemical Technology*, Fourth Edition, Vol. 18, p. 837-860, 1996, by Y. Wang. Both hole transporting molecules and polymers can be used. Commonly used hole transporting molecules, in addition to TPD and MPMP mentioned above, are: 1,1-bis[(di-4-tolylamino) phenyl]cyclohexane (TAPC); N,N'-bis(4-methylphenyl)-N,N'-bis(4-ethylphenyl)-[1,1'-(3,3'-dimethyl)biphenyl]-4,4'-diamine (ETPD); tetrakis-(3-methylphenyl)-N,N,N',N'-2,5-phenylenediamine (PDA); a-phenyl-4-N,N-diphenylaminostyrene (TPS); p-(diethylamino)benzaldehyde diphenylhydrazone (DEH); triphenylamine (TPA); 1-phenyl-3-[p-(diethylamino)styryl]-5-[p-(diethylamino)phenyl] pyrazoline (PPR or DEASP); 1,2-trans-bis(9H-carbazol-9-yl)cyclobutane (DCZB); N,N,N',N'-tetrakis(4-methylphenyl)-(1,1'-biphenyl)-4,4'-diamine (TTB); and porphyrinic compounds, such as copper phthalocyanine. Commonly used hole transporting polymers are polyvinylcarbazole, (phenylmethyl)polysilane; poly(3,4-ethylendioxythiophene) (PEDOT); and polyaniline. It is also possible to obtain hole transporting polymers by doping hole transporting molecules such as those mentioned above into polymers such as polystyrene and polycarbonate.

Optional layer 140 can function both to facilitate electron transport, and also serve as a buffer layer or anti-quenching layer to prevent quenching reactions at layer interfaces. Preferably, this layer promotes electron mobility and reduces quenching reactions. Examples of electron transport materials for optional layer 140 include metal chelated oxinoid compounds, such as tris(8-hydroxyquinolato)aluminum ($Alq_3$); phenanthroline-based compounds, such as 2,9-dimethyl-4,7-diphenyl-1,10-phenanthroline (DDPA) or 4,7-diphenyl-1,10-phenanthroline (DPA), and azole compounds such as 2-(4-biphenylyl)-5-(4-t-butylphenyl)-1,3,4-oxadiazole (PBD) and 3-(4-biphenylyl)-4-phenyl-5-(4-t-butylphenyl)-1,2,4-triazole (TAZ).

The cathode 150 is an electrode that is particularly efficient for injecting or collecting electrons or negative charge carriers. The cathode can be any metal or nonmetal having a lower work function than the first electrical contact layer (in this case, an anode). Materials for the second electrical contact layer can be selected from alkali metals of Group 1 (e.g., Li, Cs), the Group 2 (alkaline earth) metals, the Group 12 metals, the lanthanides, and the actinides. Materials such as aluminum, indium, calcium, barium, samarium and magnesium, as well as combinations, can be used.

It is known to have other layers in organic electronic devices. For example, there can be a layer (not shown) between the conductive polymer layer 120 and the active layer 130 to facilitate positive charge transport and/or band-gap matching of the layers, or to function as a protective layer. Similarly, there can be additional layers (not shown) between the active layer 130 and the cathode layer 150 to facilitate negative charge transport and/or band-gap matching between the layers, or to function as a protective layer. Layers that are known in the art can be used. In addition, any of the above-described layers can be made of two or more layers. Alternatively, some or all of inorganic anode layer 110, the conductive polymer layer 120, the active layer 130, and cathode layer 150, may be surface treated to increase charge carrier transport efficiency. The choice of materials for each of the component layers is preferably determined by balancing the goals of providing a device with high device efficiency.

It is understood that each functional layer may be made up of more than one layer.

The device can be prepared by sequentially vapor depositing the individual layers on a suitable substrate. Substrates such as glass and polymeric films can be used. Conventional vapor deposition techniques can be used, such as thermal evaporation, chemical vapor deposition, and the like. Alternatively, the organic layers can be coated from solutions or dispersions in suitable solvents, using any conventional coating technique. In general, the different layers will have the following range of thicknesses: anode 110, 500-5000 Å, preferably 1000-2000 Å; hole transport layer 120, 50-2500 Å, preferably 200-2000 Å; light-emitting layer 130, 10-1000 Å, preferably 100-800 Å; optional electron transport layer 140, 50-1000 Å, preferably 100-800 Å; cathode 150, 200-10,000 Å, preferably 300-5000 Å. The location of the electron-hole recombination zone in the device, and thus the emission spectrum of the device, is affected by the relative thickness of each layer. For examples, when an emitter, such as $Alq_3$ is used as the electron transport layer, the electron-hole recombination zone can be in the $Alq_3$ layer. The emission would then be that of $Alq_3$, and not the desired sharp lanthanide emission. Thus the thickness of the electron-transport layer must be chosen so that the electron-hole recombination zone is in the light-emitting layer. The desired ratio of layer thicknesses will depend on the exact nature of the materials used.

It is understood that the efficiency of the devices of the invention made with metal complexes, can be further improved by optimizing the other layers in the device. For example, more efficient cathodes such as Ca, Ba, Mg/Ag, or LiF/Al can be used. Shaped substrates and novel hole transport materials that result in a reduction in operating voltage or increase quantum efficiency are also applicable. Additional layers can also be added to tailor the energy levels of the various layers and facilitate electroluminescence.

The iridium complexes of the invention often are phosphorescent and photoluminescent and may be useful in other applications. For example, organometallic complexes of iridium have been used as oxygen sensitive indicators, as phosphorescent indicators in bioassays, and as catalysts. The bis cyclometallated complexes can be used to sythesize tris cyclometalated complexes where the third ligand is the same or different.

EXAMPLES

The following examples illustrate certain features and advantages of the present invention. They are intended to be illustrative of the invention, but not limiting. All percentages are mole percents, unless otherwise indicated.

Example 1

This example illustrates the preparation of a ligand parent compound (HL), 2-(2-thienyl)-5-(trifluoromethyl)pyridine.

2-thienylboronic acid (Lancaster Synthesis, Inc., 1.00 g, 7.81 mmmol), 2-chloro-5-trifluoromethylpyrdine (Adrich Chemical Co., 1.417 g, 7.81 mmol), tetrakistriphenylphosphine palladium(0) (Aldrich, 451 mg, 0.391 mmol), potassium carbonate (EM Science, 3.24 g, 23.4 mmol), water (20 mL), and dimethoxyethane (Aldrich, 20 mL) were allowed to stir at reflux for 20 hours under $N_2$, after which time the mixture was cooled to room temperature and the organic and aqueous layers were separated. The aqueous layer was extracted with 3×50 mL of diethyl ether, and the combined organic fractions were dried with sodium sulfate, filtered, and the filtrate was evaporated to dryness. The crude product was purified by silica gel flash chromatography with $CH_2Cl_2$/hexanes (1:1) as the eluent (product Rf=0.5), to afford the product as a white crystalline solid (yield=5.2 g, 73% isolated yield). $^1$H NMR ($CDCl_3$, 296K, 300 MHz): δ=7.73-7.57 (2H, m), 7.55 (1H, d, J=8.5 Hz), 7.34 (1H, d, J=4.8 Hz), 6.88 (1H, d, J=4.8 Hz) ppm. $^{19}$F NMR ($CDCl_3$, 296K, 282 MHz) δ=−62.78 ppm.

Example 2

This example illustrates the preparation of the intermediate dichloro bridged dimer, [IrCl{2-(2-thienyl)-5-(trifluoromethyl)pyridine}2]2.

2-(2-thienyl)-5-(trifluoromethyl)pyridine from Example 1 (555 mg, 2.42 mmol), iridium trichloride (Strem Chemicals, 401 mg, 1.13 mmol), 2-ethoxyethanol (Aldrich Chemical Co., 10 mL) and water (1 mL) were allowed to reflux under nitrogen for 15 hours, after which time the reaction was allowed to cool to room temperature. The resulting precipitated product was collected by filtration, washed with hexanes, and dried in vacuo, to afford 575 mg (37%) of the product as a red-orange solid. $^1$H NMR ($CDCl_3$, 296 K, 300 MHz): δ=9.30 (4H, d, J=1.5 Hz), 7.80 (4H, dd, J=2.0 Hz and 8.5 Hz), 7.59 (4H, d, J=8.5 Hz), 7.21 (8H, d, J=4.8 Hz), 5.81 (d, 4H, J=4.9 Hz). $^{19}$F NMR ($CDCl_3$, 296K, 282 MHz) δ=−62.07 ppm.

Example 3

This example illustrates the preparation of a tris-cyclometallated iridium complex, [Ir{2-(2-thienyl)-5-(trifluoromethyl)pyridine}3], compound 1-a from Table 1.

[IrCl{2-(2-thienyl)-5-(trifluoromethyl)pyridine}2]2 from Example 2 (100 mg, 0.073 mmol), 2-(2-thienyl)-5-(trifluoromethyl)pyridine from Example 1 (201 mg, 0.88 mmol), and silver trifluoroacetate (Aldrich, 40 mg, 0.18 mmol) were combined and allowed to stir at 170-180° C. under nitrogen for 10 min. Then the mixture was allowed to cool to room temperature and it was redissolved in a minimum amount dichloromethane. The solution was passed through a silica gel column with dichloromethane/hexanes (1:1) as the eluting solvent. The first red-orange fraction to come down the column (product Rf=0.5) was collected and evaporated to dryness. The residue was suspended in hexanes, and the precipiated product was filtered and washed with excess hexanes to remove any residual 2-(2-thienyl)-5-(trifluoromethyl)pyridine, to afford the product as a red-orange solid. Isolated yield≈50 mg (39%). $^1$H NMR ($CDCl_3$, 296 K, 300 MHz): δ=7.73-7.57 (6H, m), 7.55 (3H, d, J=8.5 Hz), 7.34 (3H, d, J=4.8 Hz), 6.88 (3H, d, J=4.8 Hz). $^{19}$F NMR ($CDCl_3$, 296K, 282 MHz) δ=−62.78.

Compounds 1-b through 1-f in Table 1 were made using a similar procedure.

Example 4

This example illustrates the preparation of the ligand parent compound, 1-(4-tert-butylphenyl)-isoquinoline.

4-tert-butylphenylboronic acid (Aldrich Chemical Co., 5.00 g, 30.56 mmmol), 1-chloroisoquinoline (Adrich Chemical Co., 5.44 g, 30.56 mmol), tetrakistriphenylphosphine palladium(0) (Aldrich, 800 mg, 0.69 mmol), potassium carbonate (EM Science, 12.5 g, 23.4 mmol), water (50 mL), and dimethoxyethane (Aldrich, 75 mL) were allowed to stir at reflux for 20 h under $N_2$, after which time the mixture was cooled to room temperature and the organic and aqueous layers were separated. The aqueous layer was extracted with 3×75 mL of diethyl ether, and the combined organic fractions were dried with sodium sulfate, filtered, and the filtrate was evaporated to dryness. The crude material was chromatographed on a silica gel column, first by eluting the catalyst byproduct with 4:1 hexanes/dichloromethane, and finally the product was eluted with dichloromethane/MeOH (9.5:0.5, product $R_f$=0.7). The pure product fractions were collected and dried in vacuo, to afford 4.5 g (56% isolated yield) of a light yellow solid, >95% pure NMR spectroscopy. $^1$H NMR ($CDCl_3$, 296 K, 300 MHz): δ=8.58 (1H, d, J=5.70 Hz), 8.15 (1H, d, J=8.5 Hz), 7.83 (1H, d, J=8.5 Hz), 7.5-7.7 (7H, m), 1.38 (9H, s) ppm.

Example 5

This example illustrates the preparation of the dichloro bridged dimer, IrCl{1-(4-t-Bu-phenyl)-isoquinoline}2]2.

1-(4-t-Bu-phenyl)-isoquinoline from Example 4 (1.00 g, 3.82 mmol), $IrCl_3(H_2O)_3$ (Strem Chemicals, 633 mg, 1.79 mmol), and 2-ethoxyethanol (Aldrich Chemical Co., 40 mL) were allowed to stir at reflux for 15 h, after which time the mixture was poured into an equal volume of water. The resulting orange precipitate was isolated by filtration, washed with water, and allowed to dry in vacuo. Then the solid was re-dissolved in dichloromethane and passed through a silica gel pad. The red eluted dichloromethane solution was evaporated to dryness, and the resulting solid was suspended in hexanes. The solid was isolated by filtration to afford 650 mg (49%) of a red-orange solid, >95% pure by NMR spectroscopy. $^1$H NMR (CD$_2$Cl$_2$, 296 K, 300 MHz): δ=9.37 (4H, d, J =6.5 Hz), 8.95 (4H, d, J=8.2 Hz), 8.07 (4H, d, J=8.5 Hz), 7.90 (4H, dd, J=1.4 and 8.2 Hz), 7.7-7.9 (8H, m), 6.94 (4H, dd, J=2.0 and 8.4 Hz), 6.86 (4H, d, J=6.4 Hz), 5.92 (4H, d, J=2.0 Hz), 0.81 (36H, s) ppm.

Example 6

This example illustrates the preparation of a bis cyclometallated iridium complex, [Ir(acac){1-(4-t-Bu-phenyl)-isoquinoline}$_2$], compound 1-j, from Table 1.

[IrCl{1-(4-t-Bu-phenyl)-isoquinoline}$_2$]$_2$ from Example 5 (200 mg, 0.135 mmol), sodium acetylacetonate (Aldrich, 80 mg, 0.656 mmol), and 2-ethoxyethanol (Aldrich, 5 mL) were allowed to stir at 120° C. for 10 min, then the volatile components were removed in vacuo. The residue was redissolved in dichloromethane and passed through a pad of silica gel on a sintered glass funnel with CH$_2$Cl$_2$ as the eluting solvent. The red-luminescent filtrate was evaporated to dryness to afford 190 mg (87% isolated yield) of the desired product, >95% by 1H NMR. $^1$H NMR (CDCl$_3$, 296 K, 300 MHz): δ=8.94 (2H, dd, J=2.1 and 8.2 Hz), 8.49 (2H, d, J=6.4 Hz), 8.11 (2H, d, J=8.50 Hz), 7.98 (2H, d, J=3.9 and 9.6 Hz), 7.6-7.8 (4H, m), 7.55 (2H, d, J=6.4 Hz), 6.99 (2H, d, J=2.1 and 8.5 Hz), 6.21 (2H, d, J=2.0 Hz), 5.35 (1H, s), 1.84 (6H, s), 0.95 (18H, s) ppm.

Compounds 1-g through 1-i and 1-k through 1-l in Table 1 were made using a similar procedure.

Example 7

This example illustrates the preparation of the ligand parent compound, 1-(perdeuterophenyl)-isoquinoline.

Perdeutero-benzeneboronic acid, dimethylester: To a solution of bromobenzene-d5 (Aldrich Chemical Co., 10.0 g, 61.7 mmol) in dry diethyl ether (50 mL) at −78° C. under nitrogen was added n-BuLi (Aldrich, 1.6 M in hexanes, 38.6 mL) slowly over two minutes. The stirred mixture was allowed to warm to room temperature for 2 hours, and then it was transferred to another flask which contained a stirred solution of trimethylborate (Aldrich, 50 mL, 494 mmol) and dry diethylether (200 mL) at −78° C. under N$_2$. The resulting mixture was allowed to warm to room temperature and stirred for 15 hours, after which time ice-cold 2 M HCl (50 mL) was added to quench the reaction mixture. The organic phase was separated, dried with sodium sulfate, filtered, and evaporated to dryness, to afford 4.9 g (52% yield) of the desired product as a white solid. $^1$H NMR (CDCl$_3$, 296 K, 300 MHz) δ 3.73 (br s) ppm.

1-(perdeuterophenyl)-isoguinoline: 1-Chloroisoquinoline (Aldrich Chemical Co., 5.00 g, 30.6 mmol), perdeuterobenzeneboronic acid, dimethyl ester from the synthesis above (4.87 g, 31.4 mmol), potassium carbonate (EM Science, 8.4 g, 61.2 mmol), tetrakistriphenylphosphine palladium(0) (Aldrich, 707 mg, 0.611 mmol), dimethoxymethane (Aldrich, 100 mL) and water (100 mL) were combined under nitrogen, and the mixture was allowed to reflux for 15 hours. After this time, the organic layer was separated, and the aqueous layer was extracted with 3×50 mL of diethyl ether. The combined organic components were dried with sodium sulfate, filtered, and evaporated to dryness. The resulting crude product was purified by silica gel chromatography. The phosphine catalyst was first eluted with 4:1 dichloromethane/hexanes, and then the desired product was eluted with 100% dichloromethane and then dichloromethane/methanol (95:5, product Rf=0.6). The product fractions were combined and evaporated to dryness, to afford 4.5 g (70%) of the desired product as a white solid. $^1$H NMR (CDCl$_3$, 296 K, 300 MHz): δ=8.60 (1H, d, J=5.7 Hz), 8.10 (1H, d, J=8.5 Hz), 7.88 (1H, d, J=8.4 Hz), 7.67 (2H, m), 7.53 (1H, m) ppm.

Example 8

This example illustrates the preparation of the dichloro bridged dimer, [IrCl{1-(perdeuterophenyl)-isoquinoline}$_2$]$_2$.

1-(Perdeuterophenyl)-isoquinoline from Example 7 (3.00 g, 14.3 mmol), IrCl$_3$(H$_2$O)$_3$ (Strem Chemicals, Inc.) 2.42 g, 6.80 mmol), 2-ethoxyethanol (Aldrich Chemical Co., 45 mL), and water (5 mL) were allowed to stir at reflux for 15 hours under nitrogen, after which time the resulting precipitated product was isolated via filtration. It was then washed with excess methanol, then diethyl ether, and finally dried in vacuo, to afford the desired product as a red-orange solid. Yield=2.12 g (48%).

Example 9

This example illustrates the preparation of a bis cyclometallated iridium complex, Ir(acac){1-(perdeuterophenyl)-isoquinoline}$_2$, compound 1-m, from Table 1.

[IrCl{1-(perdueterophenyl)-isoquinoline}$_2$]$_2$ from Example 8 (300 mg, 0.232 mmol), acetylacetone, sodium salt (Aldrich Chemical Co., 71 mg, 0.581 mmol), and 2-ethoxyethanol (Aldrich, 15 mL) were allowed to stir at 1200° C. for 45 min, after which time the volatile components were removed in vacuo. The resulting residue was taken up in dichloromethane and passed through a silica gel pad with dichloromethane as the eluting solvent. The first red fraction (Rf=1.0) was collected and evaporated to dryness, to afford the desired product as a red-orange solid. Yield=230 (70%). $^1$H NMR (CDCl$_3$, 296 K, 300 MHz) δ=8.99 (1H, m), 8.45 (1H, d, J=6.4 Hz), 7.98 (1H, m), 7.75 (2H, m), 7.55 (1H, d, J=6.3 Hz), 5.29 (1H, s), 1.79 (6H, s) ppm. Additional signals observed that are due to small amounts of H/D exchange that occurred in the cyclometallation reaction: 8.24 (0.5H, m), 6.96 (0.20H, d, J=9.8 Hz).

Example 10

This example illustrates the formation of OLEDs using the iridium complexes of the invention.

Thin film OLED devices including a hole transport layer (HT layer), electroluminescent layer (EL layer) and at least one electron transport layer (ET layer) were fabricated by the thermal evaporation technique. An Edward Auto 306 evaporator with oil diffusion pump was used. The base vacuum for all of the thin film deposition was in the range of 10$^{-6}$ torr. The deposition chamber was capable of depositing five different films without the need to break up the vacuum.

An indium tin oxide (ITO) coated glass substrate was used, having an ITO layer of about 1000-2000 Å. The substrate was first patterned by etching away the unwanted ITO area with 1N HCl solution, to form a first electrode pattern. Polyimide tape was used as the mask. The patterned ITO substrates were then cleaned ultrasonically in aqueous detergent solution. The substrates were then rinsed with distilled water, followed by isopropanol, and then degreased in toluene vapor for ~3 hours. Alternatively, patterned ITO from Thin Film Devices, Inc was used. These ITO's are based on Corning 1737 glass coated with 1400 Å ITO coating, with sheet resistance of 30 ohms/square and 80% light transmission.

The cleaned, patterned ITO substrate was then loaded into the vacuum chamber and the chamber was pumped down to $10^{-6}$ torr. The substrate was then further cleaned using an oxygen plasma for about 5-10 minutes. After cleaning, multiple layers of thin films were then deposited sequentially onto the substrate by thermal evaporation. Finally, patterned metal electrodes of Al were deposited through a mask. The thickness of the film was measured during deposition using a quartz crystal monitor (Sycon STC-200). All film thicknesses reported in the Examples are nominal, calculated assuming the density of the material deposited to be one. The completed OLED device was then taken out of the vacuum chamber and characterized immediately without encapsulation.

A summary of the device layers and thicknesses are given in Table 2. In all cases the anode was ITO as discussed above, and the cathode was Al having a thickness in the range of 700-760 Å.

TABLE 2

| Sample | HT layer Thickness, Å | EL layer thickness, Å | ET layer thickness, Å | Cathode thickness, Å |
|---|---|---|---|---|
| 1 | MPMP 504 | Compound 1-a 411 | DPA 418 | Al 737 |
| 2 | MPMP 513 | Compound 1-i 420 | DPA 412 | Al 737 |
| 3 | MPMP 513 | Compound 1-j 414 | DPA 400 | Al 721 |
| 4 | MPMP 530 | Compound 1-k 407 | DPA 407 | Al 732 |
| 5 | MPMP 533 | Compound 1-l 411 | DPA 414 | Al 727 |
| 6 | MPMP 563 | Compound 1-f 305 | DPA 408 | Al 725 |
| 7 | MPMP 538 | Compound 1-h 409 | DPA 418 | Al 734 |
| 8 | MPMP 526 | Compound 1-c 428 | DPA 402 | Al 728 |
| 9 | MPMP 530 | Compound 1-m 404 | DPA 415 | Al 725 |

Figure 7:
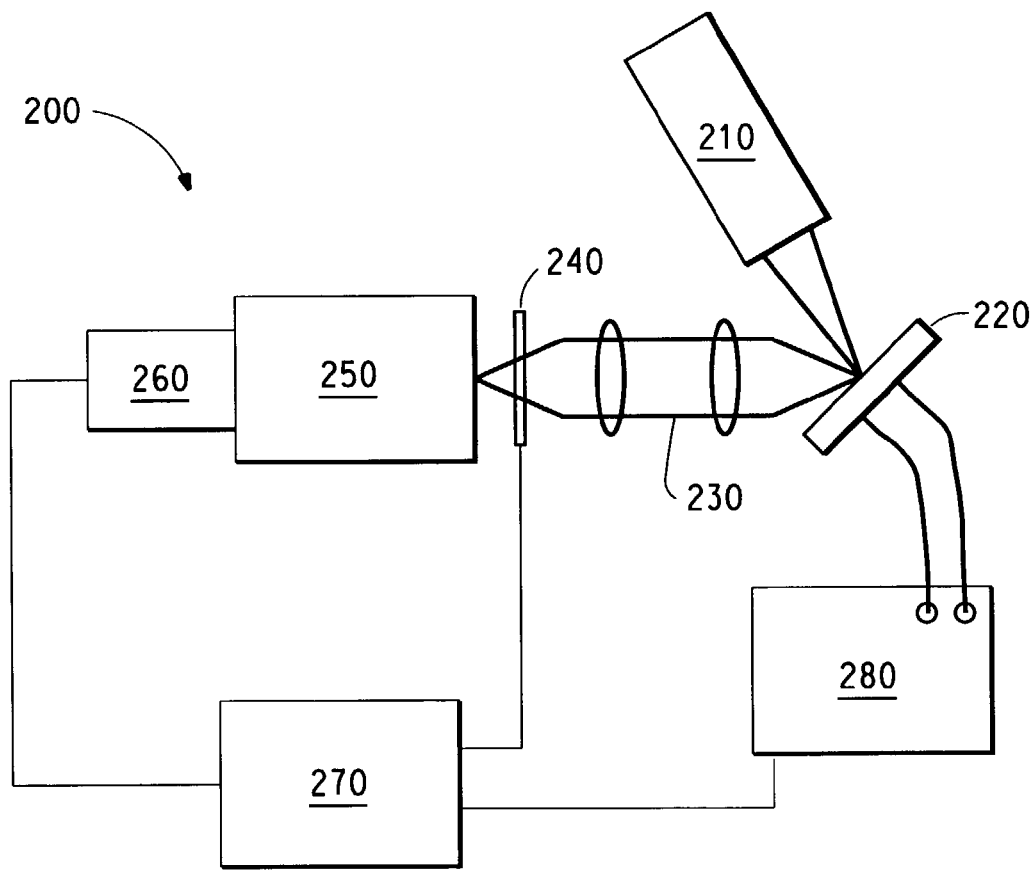
FIG. 7 is a schematic diagram of an LED testing apparatus.

DPA = 4,7-diphenyl-1,10-phenanthroline
ET = electron transport
EL = electroluminescence
HT = hole transport
MPMP = bis[4-(N,N-diethylamino)-2-methylphenyl](4-methylphenyl)methane The OLED samples were characterized by measuring their (1) current-voltage (I-V) curves, (2) electroluminescence radiance versus voltage, and (3) electroluminescence spectra versus voltage. The apparatus used, 200, is shown in FIG. 7. The I-V curves of an OLED sample, 220, were measured with a Keithley Source-Measurement Unit Model 237, 280. The electroluminescence radiance (in the unit of $Cd/m^2$) vs. voltage was measured with a Minolta LS-110 luminescence meter, 210, while the voltage was scanned using the Keithley SMU. The electroeluminescence spectrum was obtained by collecting light using a pair of lenses, 230, through an electronic shutter, 240, dispersed through a spectrograph, 250, and then measured with a diode array detector, 260. All three measurements were performed at the same time and controlled by a computer, 270. The efficiency of the device at certain voltage is determined by dividing the electroluminescence radiance of the LED by the current density needed to run the device. The unit is in Cd/A.

The results are given in Table 3 below.

TABLE 3

Electroluminescent Properties of Iridium Compounds

| Sample | Peak Radiance, $Cd/m^2$ | Peak efficiency, Cd/A | Approximate Peak Wavelengths, nm |
|---|---|---|---|
| 1 | 200 $Cd/m^2$ at 25 V | 1.5 | 570 |
| 2 | 100 $Cd/m^2$ at 22 V | 0.65 | 620 |
| 3 | 200 at 22 V | 1.2 | 625 |
| 4 | 1 at 21 V | 0.04 | >670 |
| 5 | 400 at 22 V | 1.6 | 605 and 640 |
| 6 | 5 at 20 V | 0.3 | 585 |
| 7 | 7 at 23 V | 0.06 | 620 |
| 8 | 2.5 at 23 V | 0.3 | 625 |
| 9 | 350 at 19 V | 0.6 | 625 |

Example 11

This example illustrates the formation of OLED's using a red-emission material of the invention as a dopant in a poly(fluorene) polymer matrix. The resulting blend will be used as the active red-emissive layer in an OLED. The iridium complex, [Ir(acac){1-(4-t-Bu-phenyl)-isoquinoline}$_2$], compound 1-j, from Table 1, will be prepared as described in Example 6. The polyfluorene polymer will be prepared as described in Yamamoto, Progress in Polymer Science, Vol. 17, p 1153 (1992), where the dihalo, preferably dibromo, derivatives of the monomeric units are reacted with a stoichiometric amount of a zerovalent nickel compound, such as bis(1,5-cyclooctadiene)nickel(0).

The organic film components in this OLED example will all be solution processed. Device assembly will be as follows: ITO/glass substrate (Applied Films) will be patterned (device active area=entire 3 $cm^2$) and cleaned as described in Example 10. The substrate will then be further cleaned by placing in a 300 W plasma oven for 15 min. A poly(ethylenedioxythiophene)-poly(styrenesufonic acid) (PEDOT-PSSA, Bayer Corp.) buffer layer (i.e. hole transport/injection layer) will then be spin-coated to a thickness of 90 nm. The film will be dried on a hotplate at 200° C. for 3 min. The substrate will be then transferred to a nitrogen-filled glovebox, at which point a solution of poly(fluorene) polymer, [Ir(acac){1-(4-t-Bu-phenyl)-isoquinoline}$^2$] (1.6 mmol), and anhydrous toluene (7.5 mL) will be spin coated on the substrate to a thickness of 70 nm. The substrate will be then transferred to a high vacuum chamber, where Ba (3.5 nm) followed by Al (400 nm) will be thermally deposited at 2.0×10$^{-6}$ torr. The resulting OLED device will then be sealed from air by gluing a glass slide on top of the cathode with the use of a UV-curable epoxy resin.

The device will be fully characterized by acquiring current-voltage, luminance-voltage, luminance-current, efficiency-voltage, and efficiency-current profiles. This will be accomplished with the use of a computer-driven (Labview software) Keithley Source-Measurement Unit and a photodiode, the latter which integrated light output over the entire 3 cm$^2$ device active area.

What is claimed is:

1. A compound having the formula IrL$_2$Z, wherein L is Formula III, and wherein A=N—CH$_3$, R$^5$=CF$_3$, R$^3$=R$^4$=R$^6$=H, α=0, and Z is 2,4-pentanedionate,

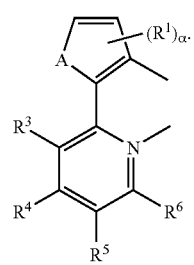
(III)

2. An organic electronic device comprising an active layer that comprises the compound of claim 1.

3. The device of claim 2 wherein the active layer further comprises a diluent.

4. The device of claim 3 wherein the diluent is selected from poly(N-vinyl carbazole); polysilane; 4,4'-N,N'-dicarbazole biphenyl; and tertiary aromatic amines.

5. An active layer comprising at least one compound having Formula II:

IrL$_2$Z (II)

wherein:

Z is selected from β-dienolates; and

L is selected from Formulae IV-VII:

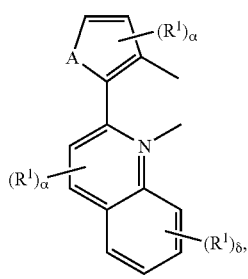
(IV)

-continued

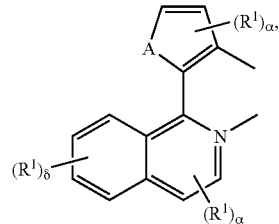
(V)

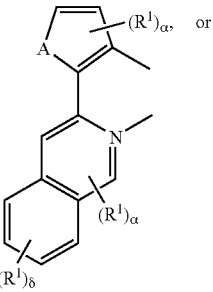
(VI)

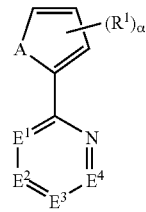
(VII)

wherein:

R$^1$ is, independently at each occurrence, selected from D, D, C$_n$H$_{2n+1}$, OR$^{11}$, SR$^{11}$, N(R$^{11}$)$_2$, F, C$_n$(H+F)$_{2n+1}$, OC$_n$(H+F)$_{2n+1}$, and OCF$_2$Y, or adjacent pairs of R$^1$ can be joined to form a five- or six-membered ring;

Y is H, Cl, or Br;

R$^{11}$ is the same or different at each occurrence and is H or C$_n$H$_{2n+1}$;

A is N—CH$_3$;

n is an integer from 1 through 12; and

α is 0, 1 or 2;

δ is 0 or an integer from 1 through 4; and

E$^1$ through E$^4$ are the same or different and are N or CR$^{12}$, with the proviso that at least one E is N; and R$^{12}$ is the same or different at each occurrence and is selected from H, D, SR$^{11}$, N(R$^{11}$)$_2$, F, C$_n$(H+F)$_{2n+1}$, OC$_n$(H+F)$_{2n+1}$, and OCF$_2$Y, or adjacent pairs of R$^{12}$ can be joined to form a five- or six-membered ring, with the proviso that at least one of R$^{12}$ is selected from D, F, C$_n$(H+F)$_{2n+1}$, OC$_n$(H+F)$_{2n+1}$, and OCF$_2$Y.

* * * * *